United States Patent

Kannenberg et al.

[11] Patent Number: 6,162,217
[45] Date of Patent: Dec. 19, 2000

[54] METHOD AND APPARATUS FOR CONTROLLING A TEMPERATURE-CONTROLLED PROBE

[75] Inventors: Donald P. Kannenberg, San Jose; Andrew I. Lisiecki, Irvine, both of Calif.

[73] Assignee: Oratec Interventions, Inc., Menlo Park, Calif.

[21] Appl. No.: 09/296,690

[22] Filed: Apr. 21, 1999

[51] Int. Cl.[7] .................................................. A61B 18/04
[52] U.S. Cl. ............................................ 606/34; 607/102
[58] Field of Search .................... 606/34, 36–40, 606/32–33

[56] References Cited

U.S. PATENT DOCUMENTS

| | | | |
|---|---|---|---|
| 5,370,645 | 12/1994 | Klicek et al. | 606/35 |
| 5,383,874 | 1/1995 | Jackson et al. | 606/1 |
| 5,569,242 | 10/1996 | Lax et al. | |
| 5,871,481 | 2/1999 | Kannenberg et al. | |
| 5,931,835 | 8/1999 | Mackey | 606/34 |
| 5,954,719 | 9/1999 | Chen et al. | 606/42 |
| 6,074,386 | 6/2000 | Goble et al. | 606/34 |

*Primary Examiner*—Linda C. M. Dvorak
*Assistant Examiner*—Roy Gibson
*Attorney, Agent, or Firm*—Flehr Hohbach Test Albritton & Herbert LLP

[57] ABSTRACT

A method and apparatus to control a power output of a probe connected to a controller in a thermal energy controller system to maintain a target temperature. The system includes a probe, a controller/generator and a means for connecting the probe to the controller. The probe has a thermal element and a temperature sensor. The temperature sensor provides a sensed temperature. The method and apparatus allow the controller to more effectively accommodate different types of probes by providing selectable probe settings for the probes. The controller modifies its operation in response to the selected probe setting. In this way, the power output of each type of probe can be more effectively controlled to better maintain the selected target temperature.

21 Claims, 10 Drawing Sheets

PID_Control procedure

FIG. 14

METHOD AND APPARATUS FOR CONTROLLING A TEMPERATURE-CONTROLLED PROBE

BRIEF DESCRIPTION OF THE INVENTION

This invention relates generally to medical devices. More particularly, this invention relates to a method and apparatus for controlling the temperature of a probe that is used to vary the thermal energy delivered to tissue during a surgical procedure.

BACKGROUND OF THE INVENTION

Soft tissue is the most abundant tissue in the human body. Most soft tissue is collagen—over 90% of the organic matter in tendons and ligaments is collagen. The connective tissue in joints is comprised of soft tissue, generally collagen tissue. When soft tissue in a joint is damaged, the healing process is often long and painful.

Well-known methods for addressing the treatment of soft tissue in injured joints include strengthening exercises, open surgery, and arthroscopic techniques. Using current treatments, many people with injured joints suffer from prolonged pain, loss of motion, nerve injury, and some develop osteoarthritis. The soft tissue in many injured joints never heals enough to return the damaged joint to its full range of function.

It is known in the art that thermal energy applied to soft tissue, such as collagen tissue, in joints may alter or manipulate the tissue to provide a therapeutic response during thermal therapy. In particular, applying controlled thermal energy to soft tissue in an injured joint can cause the collagenous tissue to shrink, thereby tightening unstable joints.

Medical probes for the rehabilitative thermal treatment of soft tissues are known in the art. Examples of these probes include laser probes and RF heated probes. While these tools meet the basic need for rehabilitative thermal treatment of soft tissues, such as collagen tissues, many suffer from temperature over-shoot and under-shoot fluctuation causing unpredictable results in the thermal alteration.

One medical probe in U.S. Pat. No. 5,458,596 to Lax, et al., discloses examples of a probe with a proximal and distal end that employs heat for the controlled contraction of soft tissue. However, a potential drawback of many prior art probes is that the probe's temperature can become unstable when heat from the probe is dissipated into the mass of the treated tissue. This situation can be a particular problem when treating dense tissue; dense tissue acts as a heat sink thereby requiring additional energy input to maintain the desired temperature. The application of additional energy in an attempt to compensate for the heat sink effect can cause an underdamped effect before settling out at the correct temperature.

In general, a system is overdamped when its damping factor is greater than one and has a slow response time. A system is critically damped when its damping factor is exactly one. A system is underdamped when its damping factor is less than one. In an underdamped system, "ringing" is a problem because it can cause the momentary application of temperatures that are too high for the safe heating of soft tissue. When this occurs, damage to the soft tissue may result from charring, ablation or the introduction of unwanted and harmful effects on the soft tissue causing injury.

Typically, the medical probes are attached to a controller to control the power output of the probe based on an actual temperature measurement from a temperature sensor such as a thermocouple in the probe and a set predetermined target temperature. The controller is part of a system that includes circuitry to monitor sensed temperature from the temperature sensor. Temperature-controlled probes are designed to provide precise coagulation to eliminate damage, charring, and bubbles. Different size probes with various configurations are available to treat various joint sizes including the shoulder, knee, ankle, wrist and the elbow.

Precise temperature control of the system in which the probes are used is required during various types of thermal therapy of soft tissue. For example, during hyperthermia which is defined as the treatment of diseased soft tissue by raising the bodily temperature by physical means, some prior art probes have difficulty in providing smooth and consistent heating because the preferred materials for the energy delivery electrodes are highly thermally responsive materials. Such materials generally do not retain large amounts of heat energy. At initiation, the controller rapidly heats the probe to achieve the target temperature which can result in an overshoot problem. During application, contact with large tissue masses tends to cause underdamped fluctuations in the probe temperature due to vast differences in the temperature of the surrounding tissue mass. Likewise, one skilled in the art will appreciate that similar problems may occur during a desired reduction in the soft tissue temperature.

In addition, different probes have different operating characteristics. Applications using larger probes typically need relatively large amounts of power to reach and maintain the desired temperature. Applications using smaller probes, such as a spine probe, need a well-controlled and precise stable temperature. However, the typical controller uses the same method to control the power output of all the different probes and does not change its control process in response to different types of probes further contributing to overshoot and undershoot problems.

Therefore, a method and apparatus are needed that allows the controller to change operation in response to the type of probe attached. This method and apparatus should also reduce temperature overshoot and oscillation while initiating and applying treatment.

SUMMARY OF THE INVENTION

A method and apparatus control the power output to a probe to maintain a target temperature. The probe is part of a system including a means for connecting a probe to a controller. The probe has a thermal element and a temperature sensor. The temperature sensor provides a sensed temperature. The method and apparatus allows the system and the controller to more effectively accommodate different types of probes by providing at least one selectable probe setting for the probes. The controller modifies its operation in response to the selected probe setting. In this way, the power output of the probe is more effectively controlled to maintain the target temperature.

A memory provides at least one set of probe settings. The set includes at least one gain parameter and corresponds to predetermined operating characteristics for a probe. A target temperature is received. A first probe setting corresponding to a desired set of operating characteristics for a probe is also received. A set of probe settings is selected in response to the first probe setting. An error signal is generated by comparing the sensed temperature to the target temperature. An output control signal is determined by applying a control function to the error signal. The control function uses the gain parameter from the selected set of probe settings. An amount of power is supplied to the thermal element in response to the output control signal.

BRIEF DESCRIPTION OF THE DRAWINGS

For a better understanding of the invention, reference should be made to the following detailed description taken in conjunction with the accompanying drawings, in which.

Like reference numerals refer to corresponding parts throughout the drawings.

DETAILED DESCRIPTION OF THE INVENTION

Figure 1:
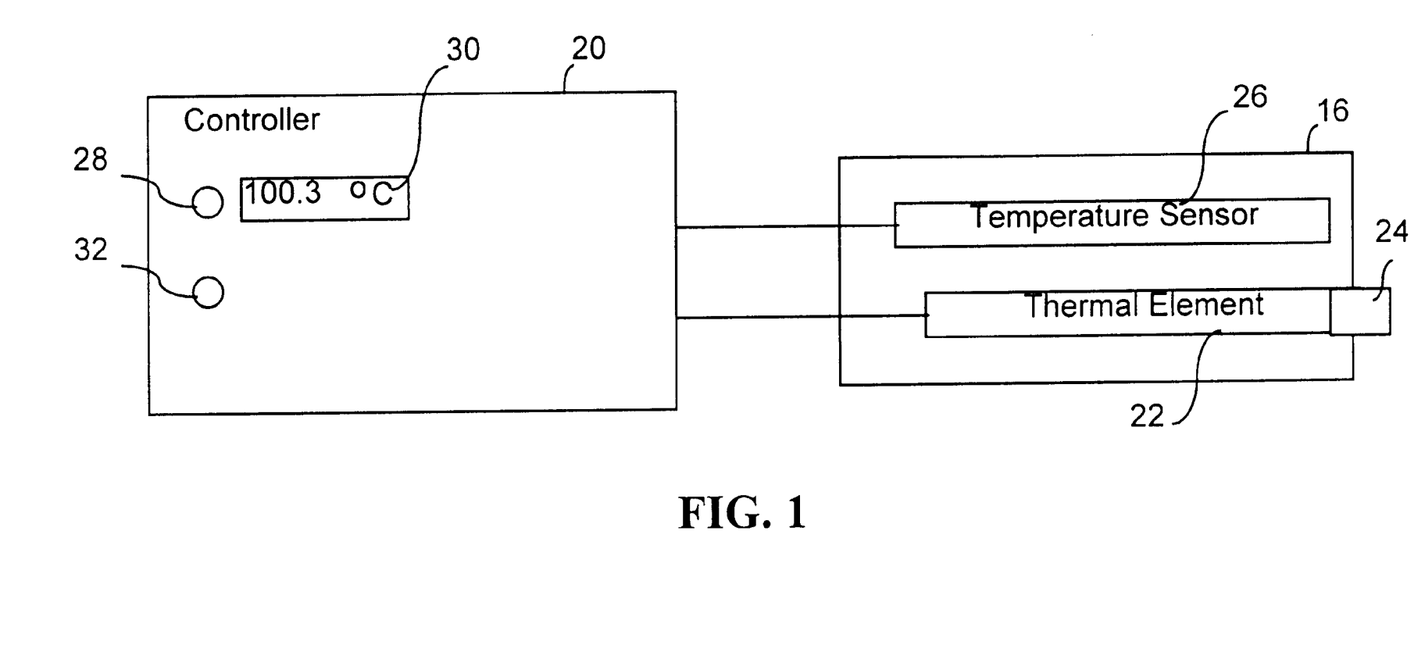
FIG. 1 illustrates a controller and probe in accordance with an embodiment of the present invention.

In FIG. 1, a probe 16 is attached to a temperature controller 20 of the present invention. The temperature controller 20 may also be defined as a generator. The probe 16 has a thermal element 22 attached to a probe tip 24. The thermal element 22 provides a means of altering the temperature of tissue by heating or cooling. The thermal element 22 includes any of the following: a transducer that delivers RF energy to the tissue, a resistive heating element that delivers thermal energy to the tissue, or a cooling element. Examples of probes and energy delivery are set forth in greater detail in U.S. Pat. No. 5,458,596 to Lax et al. which is incorporated herein by reference. The cooling element includes a means for cooling with liquid nitrogen, or a Peltier cell. A temperature sensor 26, such as a thermocouple, senses the surrounding temperature. The controller 20 receives the sensed temperature from the temperature sensor 26 and controls the amount of power that is supplied to the thermal element 22 to change the temperature of the probe tip 24 or to change the temperature of the tissue such as during the delivery of RF energy to the tissue.

In a preferred embodiment, the temperature controller 20 is part of a medical system used by physicians to adjust thermal energy to soft tissue. To set a target temperature, a physician activates a control 28, such as a knob or a digital switch, on the controller 20. The target temperature is displayed on a display 30 in degrees Celsius. To select the operating characteristics of the controller, the physician adjusts a multiposition switch 32, such as a thumbwheel switch. The operating characteristics are determined by the type of probe 16 and the type of tissue subject to thermal therapy. In other words, each switch position is associated with a probe and tissue combination. The physician may obtain the desired operating characteristics, and therefore switch position, from the manufacturer of the controller 20. Such information may be included in the instructions for use (IFU). In this way the physician can set both the temperature and operating characteristics for different probes.

Figures 2, 3:
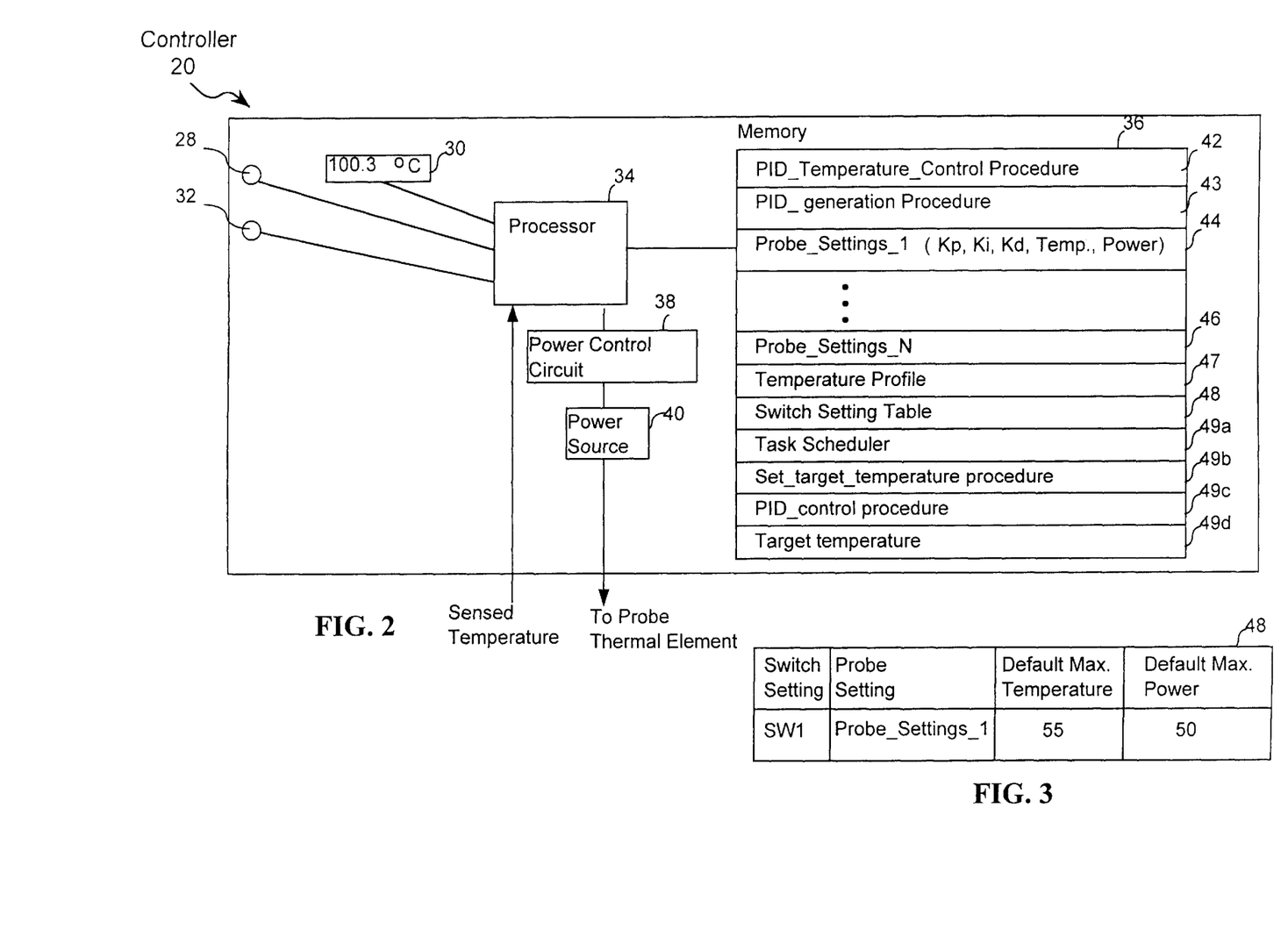
FIG. 2 illustrates the controller of FIG. 1 in accordance with an embodiment of the present invention.
FIG. 3 illustrates an exemplary table, stored in the memory of FIG. 2, associating a particular probe setting with a particular switch position.

FIG. 2 illustrates the controller 20 in more detail. A processor 34 communicates with a memory 36 the control 28, the display 30, the multiposition switch 32, and a power control circuit 38 which controls a power source 40 which is attached to the probe. The processor 34 includes a microprocessor and peripheral ports that attach to the control 28, display 30, the multiposition switch 32 and the power control circuit 38. The memory 36 includes semiconductor memory. In an alternate embodiment, the memory 36 includes disk memory.

The memory 36 stores a PID_Temperature_Control procedure 42 and a PID_generation procedure 43, which will be described below, sets of probe settings, Probe_Settings_1 to Probe_Settings_N, 44 to 46, respectively, a Temperature Profile 47, and a Switch Setting Table 48. An exemplary probe setting 46 includes a proportional gain factor Kp, an integral gain factor Ki and a derivative gain factor Kd. In addition, the exemplary probe setting 46 may also include a default target temperature and a default maximum power value. The processor 34 executes the PID_Temperature_Control procedure 42 to control the probe temperature using a PID control methodology that is implemented in the PID_generation procedure 43.

Table 1 below shows a preferred set of gain settings.

TABLE 1

| Gain Settings | | | |
|---|---|---|---|
| Gain Set | Proportional Gain Kp | Integral Gain Ki | Derivative Gain Kd |
| A | 0.031 | 0.008 | 0.008 |
| B | 0.063 | 0.016 | 0.016 |
| C | 0.125 | 0.031 | 0.031 |
| D | 0.250 | 0.125 | 0.063 |
| E | 0.500 | 0.250 | 0.125 |

The higher gain settings (D and E) are beneficial in an application in which the physician is heating a large area of tissue and must move the probe across the tissue. A greater degree of temperature oscillation may be tolerated due to the larger mass of tissue available to absorb the variations.

The lower gain settings (A, B and C) are beneficial in an application where the probe is stationary for long periods of time and the temperature is varied slowly, over minutes. The lower gain settings provide more precise temperature control.

The memory of FIG. 2 also stores a Task_scheduler 49a, a Set_target_temperature procedree 49b, a PID_control procedure 49c and a target_temperature 49d which will be explained below with reference to FIGS. 12, 13 and 14.

In the FIG. 3, the switch setting table 48 associates each multiposition switch setting with a set of probe settings.

Table 2, below, shows the exemplary switch settings of table 48 of FIG. 3. Table 2 summarizes the relationship between various switch positions, the default temperature, the default maximum output power, gain settings and probe type.

TABLE 2

| | Switch Settings | | | |
|---|---|---|---|---|
| Switch Position | Default Temperature (° C.) | Default Maximum Power (W) | Gain Set (See Table 1) | Probe Type |
| 0 | 55 | 50 | C | small |
| 1 | 55 | 40 | C | small |
| 2 | 55 | 30 | C | small |
| 3 | 55 | 20 | C | small |
| 4 | 67 | 30 | C | large |
| 5 | 67 | 40 | C | large |
| 6 | 67 | 50 | C | large |
| 7 | 60 | 30 | C | large |
| 8 | 60 | 40 | C | large |
| 9 | 60 | 50 | C | large |
| 10 | 55 | 20 | D | small |
| 11 | 55 | 30 | D | small |
| 12 | 67 | 40 | D | large |
| 13 | 67 | 50 | D | large |
| 14 | 80 | 40 | D | large |
| 15 | 80 | 50 | D | large |

Figure 4:
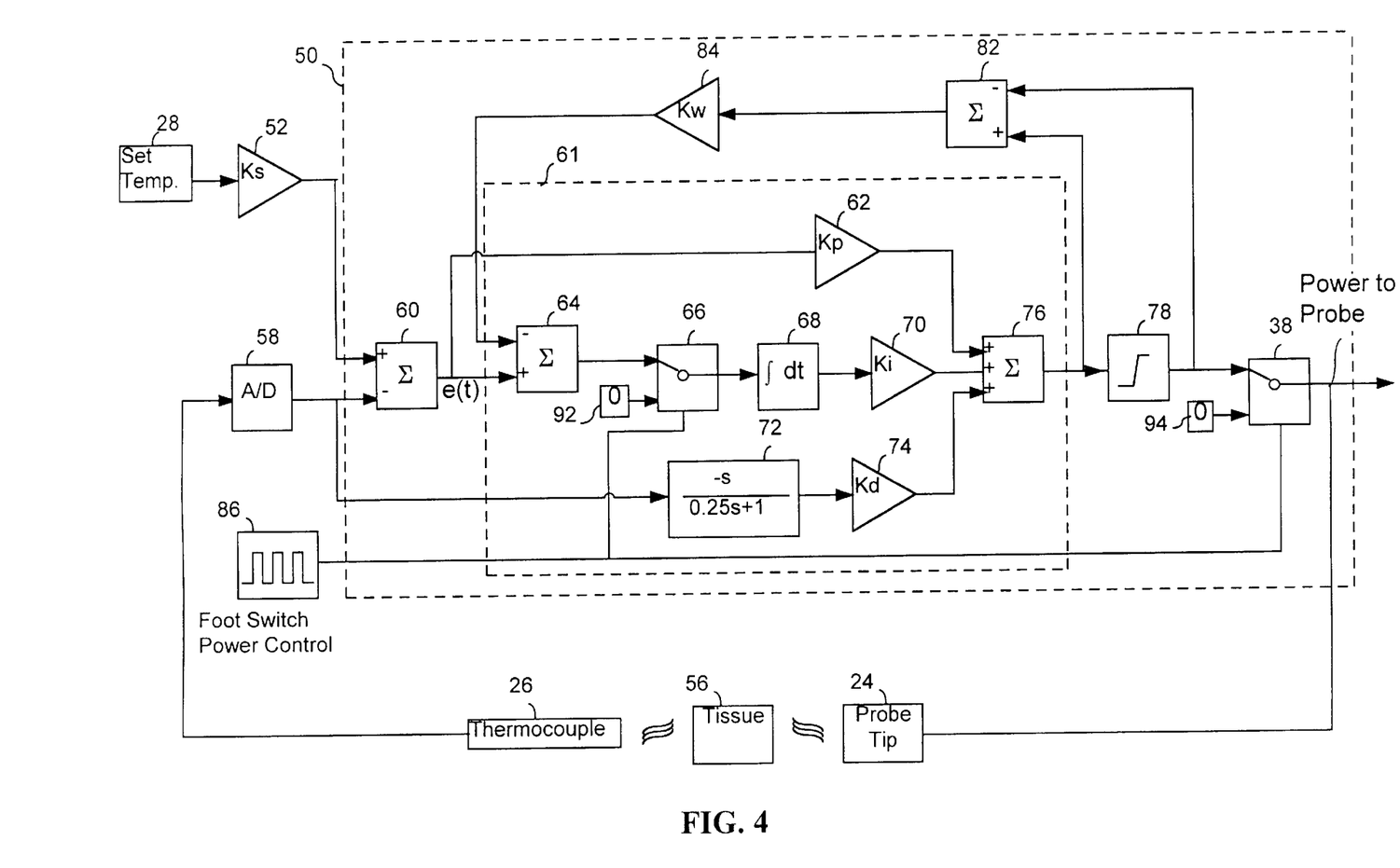
FIG. 4 illustrates one embodiment of a proportional-integral-derivative (PID) control function of the present invention.

In FIG. 4, a hardware implementation of one embodiment of a proportional-integral-derivative (PID) temperature control is illustrated, in which block 50 identifies the components of a hardware implementation which accomplishes the method of the present invention. For ease of illustration, the invention will be described with respect to a hardware implementation. A person skilled in the art will appreciate that a software implementation may also be used based on the disclosure herein. In a preferred embodiment, the temperature control block 50 is implemented in software in the PID_Temperature_Control procedure 42. The hardware implementation and various embodiments will first be discussed, followed by a discussion of the software using flowcharts.

On the controller, the physician sets the temperature using the control 28 with associated circuitry which outputs a digital target temperature signal. The digital target temperature signal is multiplied by a constant gain value, Ks, by amplifier 52. The constant gain value is typically ten.

During operation, the probe tip 24 alters the temperature of the tissue 56. The thermocouple 26 senses the surrounding change in temperature and outputs an analog sensed temperature signal corresponding to the sensed temperature. An analog-to-digital (A/D) converter 58 converts the analog sensed temperature signal to a digital sensed temperature value. The A/D converter 58 is also calibrated to multiply the sensed temperature signal by a predetermined value, such as ten to match the temperature signal.

A first summer 60 subtracts the digital sensed temperature value from the digital target temperature value to generate an error value or error signal, e(t).

A PID generation block 61 generates three signals or values-a proportional value, an integral value and a derivative value. In the software implementation, the PID generation block 61 is implemented using the PID_generation procedure 43 of FIG. 2.

To generate a proportional signal or value, a first amplifier 62 multiplies the error value by the proportional gain factor Kp.

To generate the integral value or signal, a second summer 64 subtracts an anti-integral windup signal from the error signal and supplies its output via a switch 66 to an integrator 68 which integrates the adjusted error value, as represented by the 1/s Laplace transform, to generate an intermediate value or signal. In a digital implementation, the integrator 68 can use any of the following well-known algorithms including the trapezoidal, Euler, rectangular and Runge-Kutta algorithms. A second amplifier 70 multiplies the intermediate value by the integral gain factor Ki to generate the integral value.

To generate the derivative value, the derivative unit 72 applies a transfer function to the sensed temperature value to generate an intermediate derivative signal or value. A third amplifier 74 multiplies the intermediate derivative signal or value by the derivative gain factor Kd. The transfer function will be discussed in detail below and is represented as a Laplace transform as follows:

$$\frac{-s}{0.25s+1}$$

A third summer 76 adds the proportional value, the integral value and the derivative value to generate a PID control value or signal.

According to a preferred embodiment of the present invention, the proportional gain factor, the integral gain factor, and the derivative gain factor are determined from the multiposition switch setting, the table and the sets of settings in the memory before starting the PID control operation. In this way, the PID control function and gains of the proportional, integral and derivative values can be customized to different types of probes.

A clamping circuit 78 determines if the PID control value exceeds a predetermined threshold to output an adjusted PID control value. If so, the clamping circuit 78 outputs a maximum allowed power value to the power control circuit 38 to limit or clamp the amount of power supplied to the probe to prevent overheating. Otherwise, the clamping circuit 78 outputs the PID control value. In one embodiment, the PID_Temperature_Control procedure determines the default maximum allowed power from the default maximum power value of table 48 of FIG. 3. In an alternate embodiment, the physician sets the maximum allowed power.

An antiwindup circuit also helps to limit the amount of power by preventing the integrator from including large power surges, thereby allowing the integrator to more effectively output a stable steady state value and therefore a more stable operating temperature of the probe. A fourth summer 82 subtracts the adjusted PID control value from the PID control value to generate an antiwindup difference. A fourth amplifier 84 multiplies the antiwindup difference by an antiwindup gain factor Kw, typically four, to generate an antiwindup error. The second summer 64 subtracts the antiwindup error from the error value.

Since the adjusted PID control value is typically equal to the PID control value, the antiwindup difference is typically zero and the error value supplied to the integrator 68 is not affected. When the PID control value is large, for example when power is first turned on, the PID control value may exceed the maximum allowable power and the PID control value will be clamped. In this case the antiwindup difference will be greater than zero and a positive value will be supplied to the positive input of the second summer 64 to reduce the magnitude of the error value supplied to the integrator, thereby reducing the effect of large surges.

The physician uses a foot switch 86 to control the amount of power that is supplied to the probe. The foot switch power control 86 controls the switch position of switches 66 and 38. When the foot switch power control 86 is not engaged, a zero value is supplied to the integrator 68 via the zero block 92 at a first switch position. Similarly, another zero block 94 is used by the power control circuit 38 such that no power is output to the probe. When the foot switch power control 86 is engaged, switch 66 changes to a second switch position and allows the output of the second summer 64 to flow to the integrator 68. In addition, switch 38 changes to a second switch position and allows the output control value to flow from the clamping circuit 78 to the probe.

Figure 5:
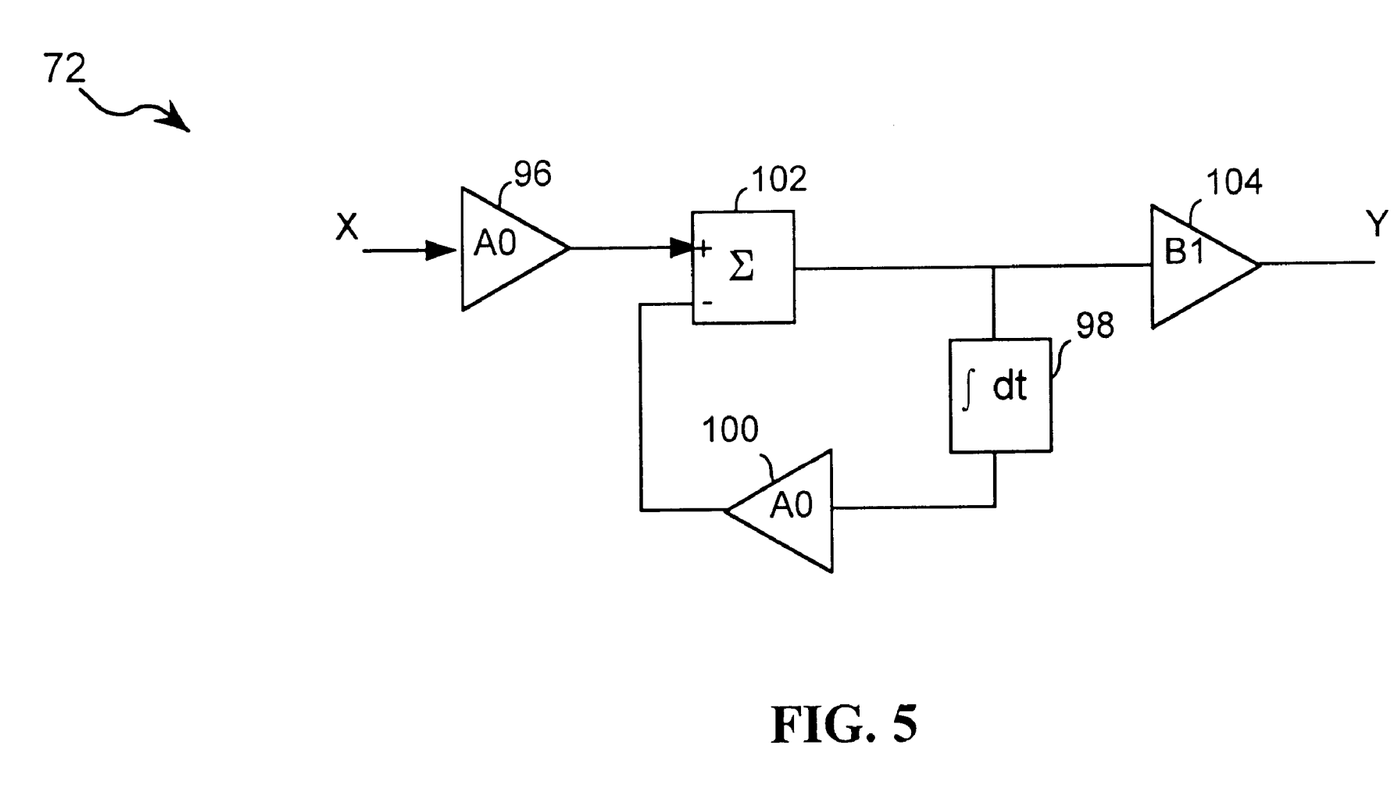
FIG. 5 illustrates an embodiment of the derivative operation of FIG. 4.

In FIG. 5, the derivative unit 72 implementing the transfer function described above is shown. The derivative unit 72 receives an input signal X and outputs a value Y. A fifth amplifier 96 multiplies the input signal X by a value A0. The derivative unit 72 includes an integrator 98 that dampens the effect of the derivative function thereby reducing the sensitivity of the derivative unit 72 to large changes in the input signal and to noise. In a digital implementation, the integrator 98 can use any of the following well-known algorithms including the trapezoidal, Euler, rectangular and Runge-Kutta algorithms. At power on, the integrator 98 output is initialized to zero. A sixth amplifier 100 multiplies the integrator output by A0 to generate a modified integrated signal. A fifth summer 102 subtracts the modified integrated signal from the multiplied input signal. A seventh amplifier 104 multiplies the output of the fifth summer 102 by B1 to generate the intermediate integrated value. In a preferred embodiment, A0 is equal to four and B1 is equal to one.

Figure 6:
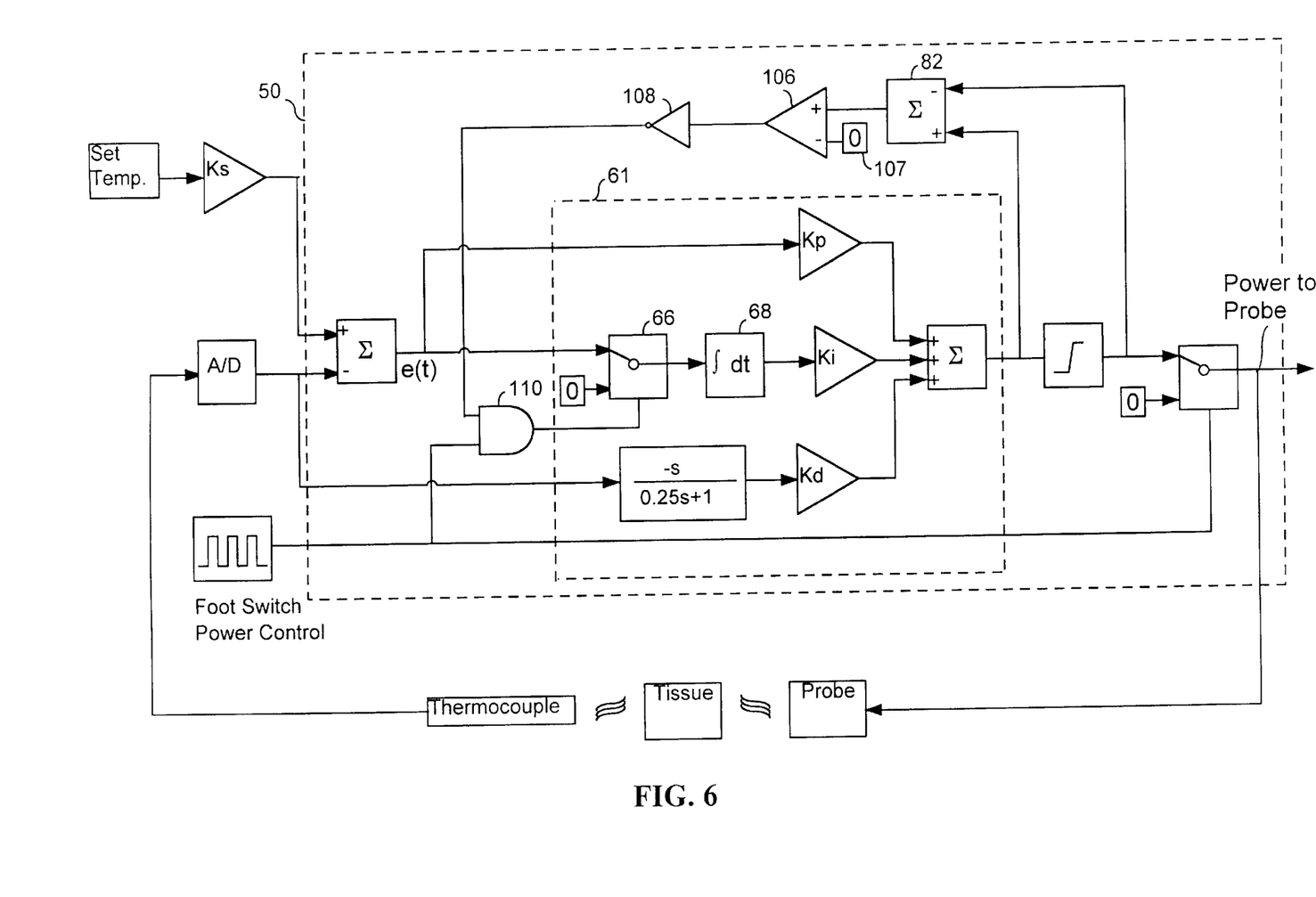
FIG. 6 illustrates a second embodiment of a PID control function of the present invention.

FIG. 6 is similar to FIG. 4, except that the antiwindup function is implemented differently. This implementation uses the antiwindup difference as a switch to stop the integrator from integrating, thereby resulting in an improved steady state operation. When the antiwindup difference is equal to zero the integrator 68 integrates. When the antiwindup difference is not equal to zero, the integrator 68 stops integrating.

As described above, the fourth summer 82 generates the antiwindup difference. A comparator 106 compares the antiwindup difference to a zero value 107. An inverter 108 inverts the output by the comparator 106. In response to the output of the inverter 108 and a signal from the foot switch, the AND gate 110 generates a position control signal that controls switch 64.

In particular, when the foot switch is not engaged by the physician, the foot switch power control signal is a zero value, the AND gate 110 outputs a digital zero value, and the switch 64 moves to the first switch position to output a zero value, thereby preventing the integrator 68 from integrating.

When the foot switch is engaged, the foot switch power control signal is a digital one value and the AND gate 110 will respond to the antiwindup circuit. When the antiwindup difference is equal to zero, the comparator 106 outputs a digital zero value which is inverted to a digital one value by inverter 108. Since the inverter 108 is outputting a digital one value, the AND gate 110 outputs a digital one value and switch 64 is positioned at the second switch position, as shown in FIG. 6, and the integrator 68 integrates the error signal e(t).

When the antiwindup difference is not equal to zero, the antiwindup difference is a positive value, the comparator 106 outputs a digital one value and the inverter 108 outputs a zero value. In response to the zero value from the inverter 108, the AND gate 110 outputs a digital zero value and switch 64 is positioned at the first switch position to output the zero value to the integrator 68, thereby preventing the integrator 68 from integrating.

Figure 7:
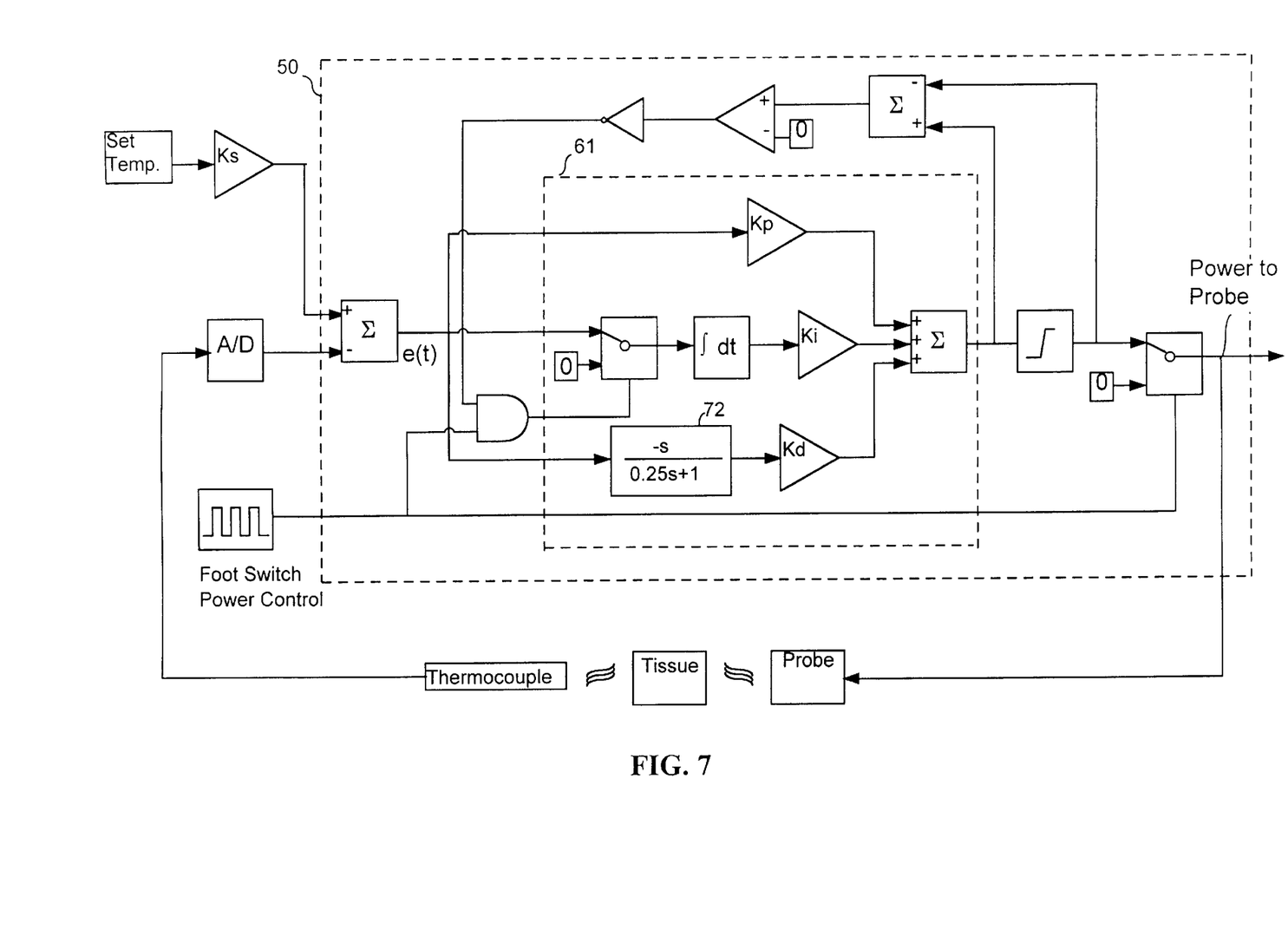
FIG. 7 illustrates a third embodiment of a PID control function of the present invention.

FIG. 7 is similar to FIG. 6 except that the error signal e(t) is supplied to the derivative block 72.

Figure 8:
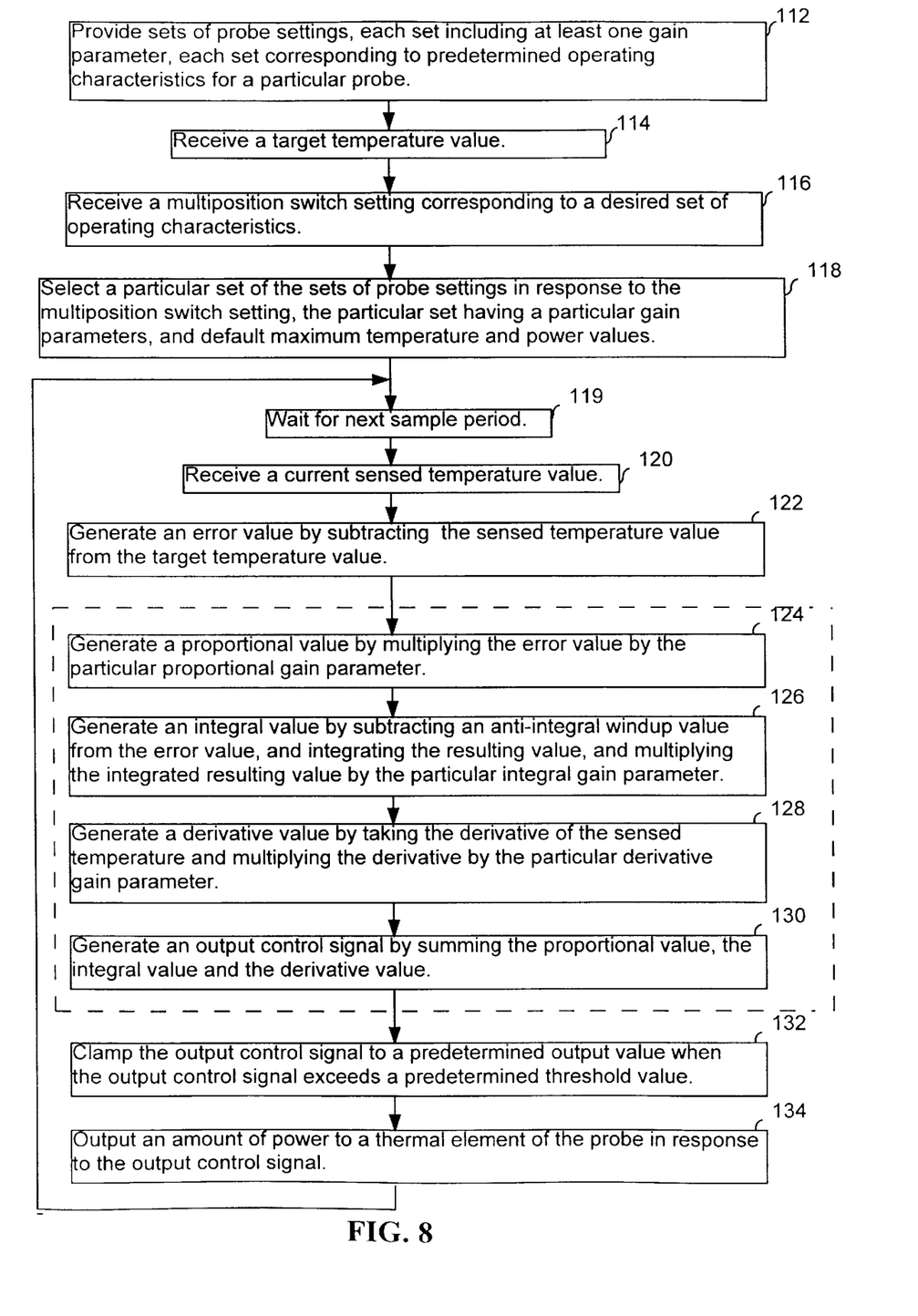
FIG. 8 is a flowchart of the PID control function of FIG. 4.

FIG. 8 is a flowchart of the PID_Temperature_Control procedure 42 of FIG. 2 that implements the PID control method of FIG. 4. In step 112, sets of probe settings and a table associating the probe settings with switch settings are provided in the memory, as described above. Each set corresponds to predetermined operating characteristics for a particular probe. In step 114, the PID_Temperature_Control procedure 42 receives a target temperature. The target temperature can be set by the physician in degrees Celsius. The target temperature value used by the PID temperature controller is the temperature set by the physician in degrees Celsius multiplied by a factor, such as ten. In step 16, the PID_Temperature_Control procedure 42 receives a first setting corresponding to a desired set of operating characteristics from the multiposition switch. In step 118, the PID_Temperature_Control procedure 42 selects a particular set of the sets of probe settings in response to the multiposition switch setting. The particular set has the 10 proportional, integral and derivative gain factors, Kp, Ki and Kd, respectively, as described above, that will be used by the PID_generation procedure. If the physician has not set a target temperature, the default target temperature that is stored in memory for the selected switch setting is used. In step 119, the PID_Temperature_Control procedure waits a predetermined amount of time before the next sample period. In one embodiment the predetermined amount of time is equal to twenty milliseconds. In other words, the PID_Temperature_Control procedure samples the sensed temperature value output by the probe every twenty milliseconds. In one implementation, the PID_Temperature_Control procedure uses interrupts to trigger the sample periods. In step 120, a sensed temperature value is received. Similar to the target temperature, the sensed temperature value represents the actual temperature in degrees Celsius and multiplied by a factor of ten. In step 122, an error value is generated by subtracting the sensed temperature from the target temperature.

As shown by the dashed lines, steps 124 to 130 are implemented in the PID_generation procedure 43 of FIG. 2 which is invoked by the PID_Temperature_Control procedure. The PID_generation procedure also corresponds to the PID generation block 61 of FIG. 4. In step 124, a proportional value is generated by multiplying the error value by the particular proportional gain parameter, Kp. In step 126, an integral value is generated by subtracting the anti-integral windup value from the error value, integrating the resulting value of the subtraction and multiplying the integrated adjusted error value by the particular integral gain parameter, Ki. The integrator 68 can be implemented with any of the following well-known algorithms including the trapezoidal, Euler, rectangular and Runge-Kutta algorithms. In step 128, a derivative value is generated by applying a derivative transfer function to the sensed temperature value, as described above, and multiplying the result of the transfer function by the particular derivative gain parameter. In step 130, an output control signal is generated by summing the proportional value, the integral value and the derivative value.

In step 132, the output control signal is clamped to a predetermined output value when the output control signal exceeds a predetermined threshold value. The predetermined threshold value is the default set power from table 2. The predetermined threshold value can be set by the physician. Alternately, based on the multiposition switch setting, the default maximum power value stored in one of the tables, described above, is used. In step 134, an amount of power is output to the thermal element of the probe in response to the output control signal, and the process repeats at step 120.

Figure 9:
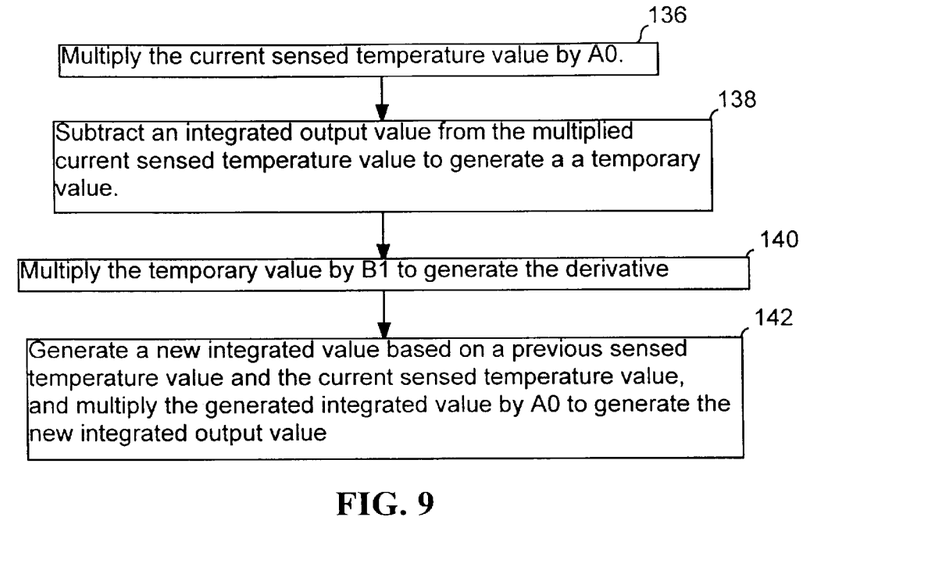
FIG. 9 is a flowchart of the derivative operation of FIG. 5 that is used in step 128 of FIG. 8.

FIG. 9 is a detailed flowchart of step 128 of FIG. 8 which generates the derivative value. In step 136, the current sensed temperature value is multiplied by a first constant, A0. In step 138, subtract an integrated output value from the multiplied current sensed temperature to generate a temporary value. Initially, the integrated output value is zero and is modified with each current sensed temperature reading. In step 140, the temporary value is multiplied by a second constant, B1, to generate the derivative value. In step 142, a new integrated value is generated based on a previous sensed temperature value and the current sensed temperature value. The integration can be performed using any of the following well-known algorithms including the trapezoidal, Euler, rectangular and Runge-Kutta algorithms. The new integrated value is multiplied by the first constant, A0, to generate another integrated output value which is used in subsequent calculations. As described above, preferably, the first constant, A0, is equal to four and the second constant, B1, is equal to one.

In an alternate embodiment of FIGS. 8 and 9, the error values are input to the derivative operation instead of the sensed temperature values.

Figure 10:
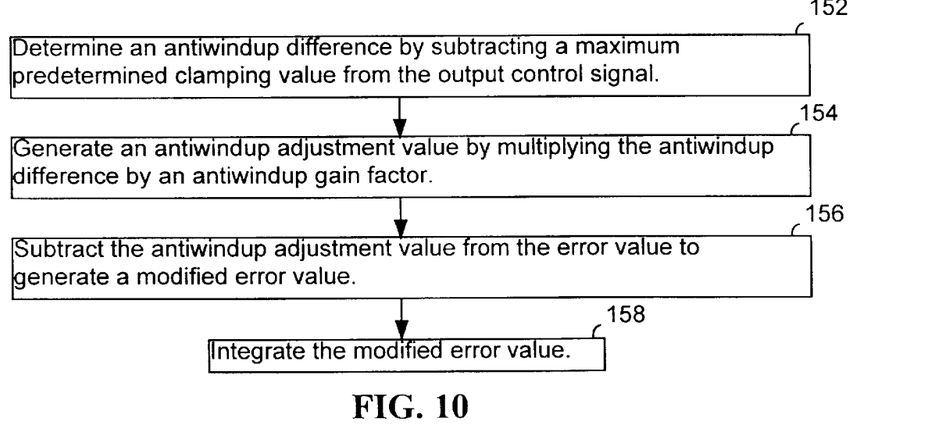
FIG. 10 is a flowchart of an antiwindup function.

FIG. 10 is a flowchart of the PID_Temperature_Control procedure 42 of FIG. 2 that implements the antiwindup function of FIG. 4. In step 152, an antiwindup difference is determined by subtracting a maximum predetermined clamping value from the output control signal. In step 154, an antiwindup adjustment value is generated by multiplying the antiwindup difference by an antiwindup gain factor. In step 156, the antiwindup adjustment value is subtracted from the error value to generate a modified error value. In step 158, the modified error value is integrated.

Figure 11:
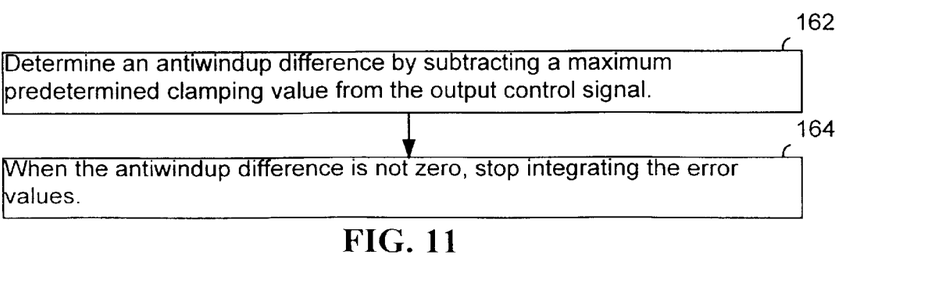
FIG. 11 is a flowchart of an alternate embodiment of an antiwindup function.

FIG. 11 is a flowchart of the PID_Temperature_Control procedure 42 of FIG. 2 that implements the alternate embodiment of the antiwindup function of FIG. 6. In step 162, an antiwindup difference is determined by subtracting a maximum predetermined clamping value from the output control signal. In step 164, when the antiwindup difference is not zero, the procedure stops integrating the error values.

Figure 12:
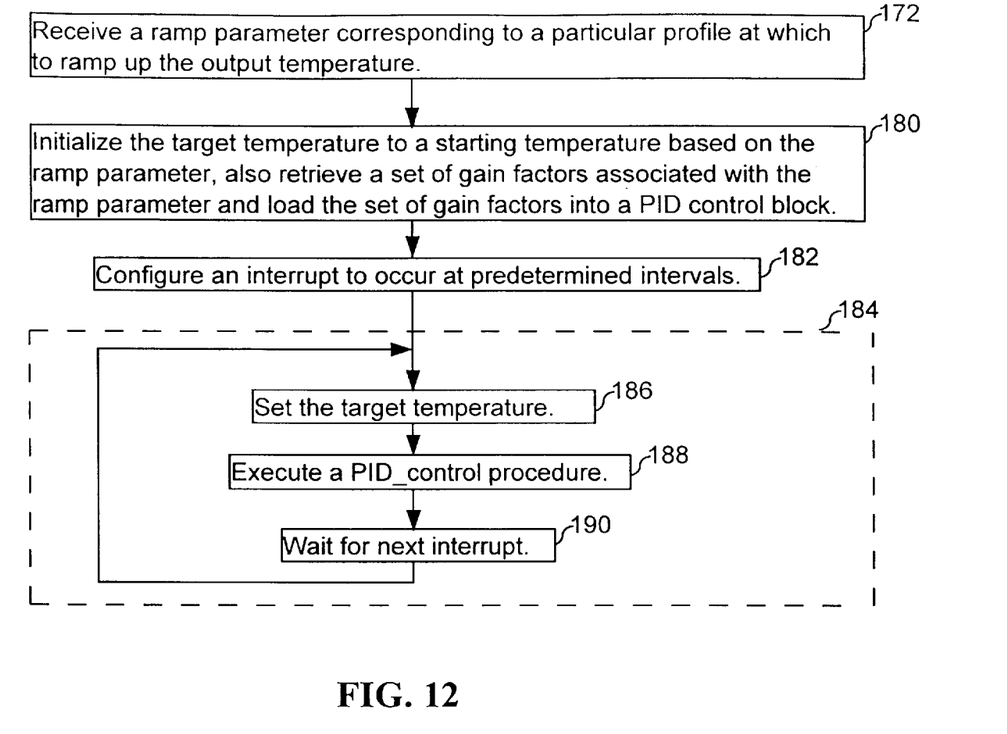
FIG. 12 is a flowchart of an embodiment which varies the target temperature to reach the final target temperature.
Figure 13:
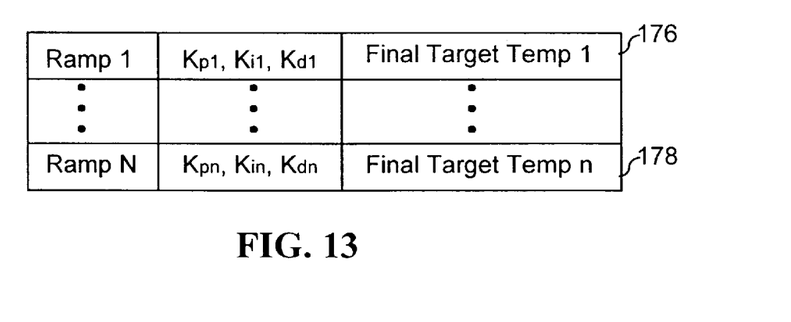
FIG. 13 is an exemplary temperature profile stored in the memory of FIG. 2.

FIG. 12 is a flowchart of the PID_Temperature_Control procedure 43 of FIG. 2 that implements variable temperature setting. Physicians may want to change the temperature profile depending on the application. When operating on large joints, the physician may want to use the probe in a high power mode to heat the probe quickly and maintain the target temperature. However, when operating on the spine, the physician may want to use a low power mode with a very controlled temperature and no overshoot.

In this embodiment of the invention, the physician via the multiposition switch can select a particular temperature profile (47, FIG. 2). The physician also may set a final target temperature. In FIG. 12, in step 172, in the PID_Temperature_Control procedure, the selected switch position corresponds to a particular temperature profile with a ramp parameter at which to ramp up the output temperature. Referring also to FIG. 13, additional exemplary temperature profiles are shown. Each profile 176, 178 stores a ramp parameter (Ramp 1, Ramp N), gain settings, and a final target temperature. Referring back to FIG. 12, in step 180, in response to the switch position, the target temperature is initialized to a starting temperature based on the ramp parameter. The set of gain factors associated with the ramp parameter are retrieved and loaded into a PID control block for use by the PID_control procedure. In step 182, the PID_Temperature_Control procedure configures the microprocessor to generate an interrupt at predetermined intervals, preferably every twenty milliseconds.

The steps in block 184 are executed in response to the interrupt. In step 186, the target temperature is set using the Set_target_temperature procedure (49b, FIG. 2). If step 186 is being executed in response to a first interrupt, the target temperature is already set to the starting temperature. Otherwise, the target temperature is changed by adding the ramp parameter to the target temperature if a predetermined amount of time has elapsed between successive target temperature changes. Preferably, the target temperature is changed every thirty seconds. If the sum of the ramp parameter and the target temperature exceeds the final target temperature, then the target temperature is set to the final target temperature.

In step 188, the PID_control procedure (49c, FIG. 2) is executed to control the temperature of the probe. The PID_control procedure is executed at each interrupt, every twenty milliseconds. The PID_control procedure will be shown in further detail in FIG. 14.

In step 190, the PID_Temperature_Control procedure waits for the next interrupt to occur.

Preferably, the microprocessor executes a task scheduler (49a, FIG. 2), such as a round-robin task scheduler, to generate the interrupts and to execute the Set_target_temperature procedure and the PID_control procedure as tasks. The target temperature is stored in the memory (49d, FIG. 2) for access by both the Set_target_temperature procedure and the PID_control procedure.

In an alternate embodiment, the Set_target_temperature procedure changes the gain factors in addition to changing the target temperature.

For example, for a particular switch position setting, a low power application with a very controlled temperature is desired. Based on the switch position, the PID_Temperature_Control procedure sets an initial target temperature that is much lower than the final target temperature. The PID_Temperature Control procedure also uses the predetermined set of gain values associated with the particular switch position setting and the interrupts are configured. In response to the interrupts, the Set_target_temperature procedure and the PID_control procedure are executed every twenty milliseconds.

After thirty seconds have passed, the Set_target_temperature procedure increments the initial target temperature by a predetermined amount, such as one degree, to generate the next target temperature. In this way, the Set_target_temperature procedure increments the intermediate target temperature until the final desired target temperature is reached. As a result, the temperature of the probe is very well-controlled and overshoot is substantially avoided.

Figure 14:
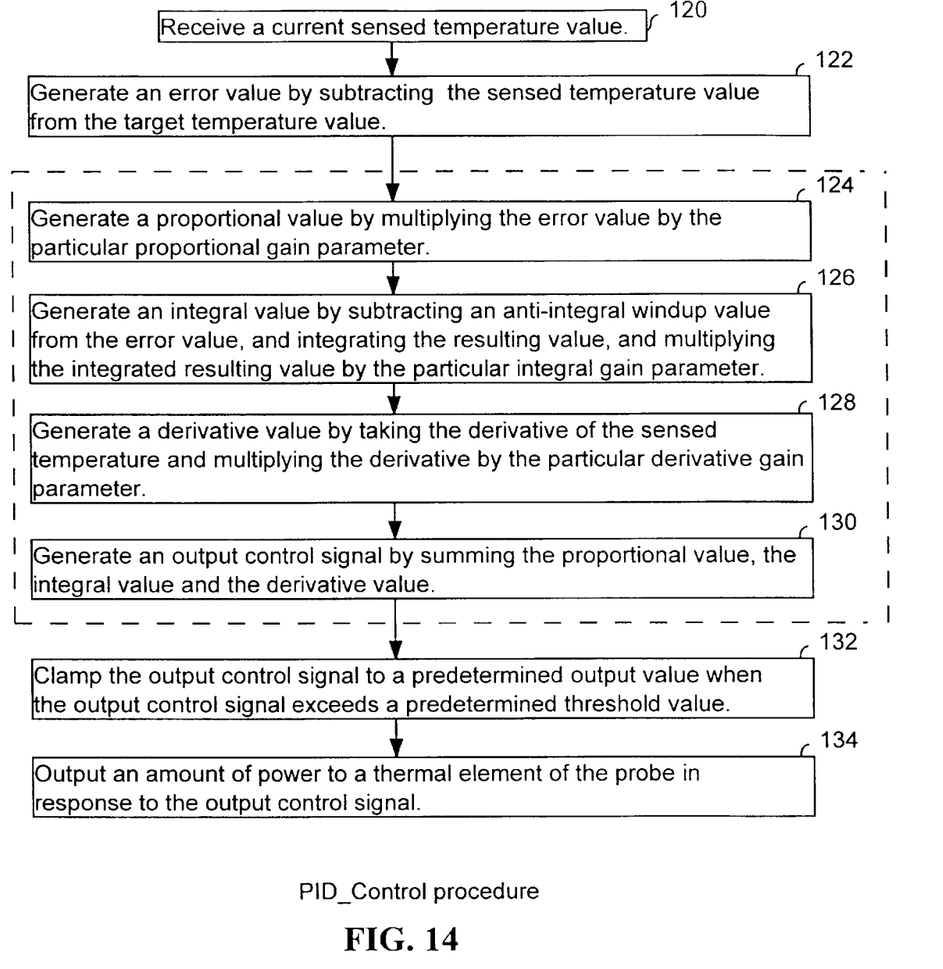
FIG. 14 is a detailed flowchart of step 188 of FIG. 13.

In FIG. 14, a flowchart of the PID_Control procedure of step 188 of FIG. 12 is shown. The PID_Control procedure uses steps 120–134 of FIG. 8, which were described above. The antiwindup adjustment of FIG. 10 or FIG. 11 can be used with the PID_Control procedure of FIG. 14.

In this way, a method and apparatus are provided that control the sensed temperature of a probe in a strictly controlled manner to avoid overdamping and underdamping. In addition, depending on the type of probe, the target temperature can be set to increase or decrease the tissue temperature. Therefore, the method and apparatus can control both high temperature and low temperature probes to heat or cool tissue.

The foregoing description, for purposes of explanation, used specific nomenclature to provide a thorough understanding of the invention. However, it will be apparent to one skilled in the art that the specific details are not required in order to practice the invention. In other instances, well known circuits and devices are shown in block diagram form in order to avoid unnecessary distraction from the underlying invention. Thus, the foregoing descriptions of specific embodiments of the present invention are presented for purposes of illustration and description. They are not intended to be exhaustive or to limit the invention to the precise forms disclosed, obviously many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated. It is intended that the scope of the invention be defined by the following Claims and their equivalents.

What is claimed is:

1. A method for controlling a power output of a probe connected to a system including controller circuitry to maintain a target temperature, the probe having a thermal element and a temperature sensor, the temperature sensor providing a sensed temperature, comprising the steps of:

providing, in a memory, at least one set of probe settings including at least one gain parameter and corresponding to predetermined operating characteristics for a particular probe;

receiving the target temperature;

receiving a first probe setting corresponding to a desired set of operating characteristics for a probe;

selecting a set from the at least one set of probe settings in response to the first probe setting;

generating an error signal by comparing the sensed temperature to the target temperature;

determining an output control signal by applying a control function to the error signal, the control function using the at least one gain parameter from the selected set; and controlling an amount of power output to the thermal element in response to the output control signal to maintain the target temperature.

2. The method of claim 1 wherein the at least one gain parameter of the at least one set of probe settings includes a set specific proportional gain factor and a set specific integral gain factor, and wherein:

said step of determining an output control signal includes the steps of:

generating a proportional signal by multiplying the error signal by the selected set specific proportional gain factor;

generating an integral signal by integrating the error signal and multiplying the integrated error signal by the selected set specific integral gain factor; and summing the proportional signal and the integral signal to generate the output control signal.

3. The method of claim 2 wherein the at least one gain parameter of the at least one set of probe settings includes a set specific derivative gain factor, and wherein:

said step of determining the output control signal includes the step of:

generating a derivative signal by applying a derivative function to the sensed temperature to generate an intermediate signal, and multiplying the intermediate signal by the selected set specific derivative gain factor, wherein said step of summing also sums the derivative signal to generate the output control signal.

4. The method of claim 1 wherein the at least one gain parameter of the at least one set of probe settings includes a set specific proportional gain factor, a set specific integral gain factor and a set specific derivative gain factor, and wherein:

said step of determining an output control signal includes the steps of:

generating a proportional signal by multiplying the error signal by the selected set specific proportional gain factor;

generating an integral signal by integrating the error signal and multiplying the integrated error signal by the selected set specific integral gain factor;

generating a derivative signal by comparing the sensed temperature to a previous sensed temperature and applying a derivative function to generate an intermediate signal and multiplying the intermediate signal by the selected set specific derivative gain factor; and summing the proportional signal, the integral signal and the derivative signal to generate the output control signal.

5. The method of claim 1 further comprising the step of:

limiting the output control signal to a predetermined output value when the output control signal exceeds a predetermined threshold.

6. The method of claim 2 further comprising the step of:

when the predetermined output value exceeds a predetermined threshold value, disabling said step of generating the integral signal.

7. The method of claim 2 further comprising the steps of:

determining an antiwindup difference by subtracting a maximum predetermined output control value from the output control signal;

generating an antiwindup adjustment signal by multiplying the antiwindup difference by an antiwindup gain factor; and generating a modified error signal by subtracting the antiwindup adjustment signal from the error signal, wherein said step of generating an integral signal integrates the modified error signal by the integral gain factor.

8. The method of claim 1 further comprising the steps of:

receiving a ramp parameter corresponding to a particular profile at which to ramp up the output power; and changing the target temperature in response to the ramp parameter.

9. The method of claim 8 further comprising the steps of:

receiving a switch setting corresponding to a particular profile at which to ramp up the output power; and changing the target temperature in response to the switch setting.

10. The method of claim 9 wherein said step of selecting the set from the at least one set of probe settings selects a first set of probe settings in response to the switch setting, and further comprising the steps of:

determining an intermediate target temperature in response to the switch setting; and selecting a second set of probe settings in response to the switch setting when the intermediate target temperature is reached.

11. The method of claim 1 wherein the at least one gain parameter of the at least one set of probe settings includes a set specific derivative gain factor, and further comprising the step of:

generating a derivative signal by multiplying the sensed temperature by a first predetermined signal, subtracting a temporary integral signal generated from a previous sensed temperature to generate an intermediate signal, and multiplying the intermediate signal by the selected set specific derivative gain factor.

12. The method of claim 1 wherein the at least one set of probe settings includes a set specific default target temperature and a set specific default maximum output power, and wherein said step of receiving the target temperature sets the target temperature to the selected set specific default target temperature, and wherein said step of controlling the amount of power output to the thermal element clamps the power output to the selected set specific default maximum output power.

13. A method for controlling a power output of a probe connected to a system including controller circuitry to maintain a target temperature, the probe having a thermal element and a temperature sensor, the temperature sensor providing a sensed temperature, comprising the steps of:

providing, in a memory, at least one set of probe settings including at least one gain parameter and corresponding to predetermined operating characteristics for a particular probe, the at least one gain parameter including a set specific proportional gain factor, a set specific integral gain factor and a set specific derivative gain factor;

receiving the target temperature;

receiving a first probe setting corresponding to a desired set of operating characteristics for a probe;

selecting a set from the at least one set of probe settings in response to the first probe setting;

receiving a sensed temperature;

generating an error signal by comparing the sensed temperature to the target temperature;

generating a proportional signal by multiplying the error signal by the selected set specific proportional gain factor;

generating an integral signal by integrating the error signal and multiplying the integrated error signal by the selected set specific integral gain factor;

generating a derivative signal by comparing the sensed temperature to a previous sensed temperature and applying a derivative function to generate an intermediate signal and multiplying the intermediate signal by the selected set specific derivative gain factor;

summing the proportional signal, the integral signal and the derivative signal to generate the output control signal;

controlling an amount of power output to the thermal element in response to the output control signal to maintain the target temperature;

determining an antiwindup difference by subtracting a maximum predetermined output control value from the output control signal;

generating an antiwindup adjustment signal by multiplying the antiwindup difference by an antiwindup gain factor; and generating a modified error signal by subtracting the antiwindup adjustment signal from the error signal, wherein said step of generating the integral signal integrates the modified error signal by the integral gain factor.

14. A system for controlling the power output of a probe connected to the system to maintain a temperature, the probe having a thermal element, and a temperature sensor providing a sensed temperature, comprising:

a processor; and a memory storing at least one set of probe settings, the at least one set including at least one gain parameter and corresponding to a predetermined operating characteristics for a particular probe, the memory also storing instructions that cause the processor to:

receive a target temperature value;

receive a first probe setting corresponding to a desired set of operating characteristics for a probe;

select a set of the probe settings in response to the first probe setting;

generate an error value by comparing the sensed temperature value to the target temperature value; and determine an output control value by applying a control function to the error value, the control function using the at least one gain parameter from the selected set whereby an amount of power is outputted to the thermal element in response to the output control value to maintain the temperature.

15. The system of claim 14 wherein the at least one gain parameter of the sets of probe settings includes a set specific proportional gain factor and a set specific integral gain factor, and wherein:

the instructions that determine the output control value includes instructions to:

generate a proportional value by multiplying the error value by the selected set specific proportional gain factor;

generate an integral signal by integrating the error value and multiplying the integrated error value by the selected set specific integral gain factor;

generate a derivative value by comparing the sensed temperature value to a previous sensed temperature value and applying a derivative function to generate an intermediate value and multiplying the intermediate value by the selected set specific derivative gain factor; and sum the proportional value, the integral value and the derivative value to generate the output control value.

16. The system of claim 14 wherein the memory further includes instructions to limit the output control value to a predetermined output value when the output control value exceeds a predetermined threshold.

17. The system of claim 14 wherein the memory further includes instructions to:

receive a switch setting corresponding to a particular profile at which to ramp up the output power; and change the target temperature in response to the switch setting.

18. A computer program product for controlling a power level of a probe connected to a medical device computer system, the computer program product for use in conjunction with the computer system, the computer program product comprising a computer readable storage medium and a computer program mechanism embedded therein, the computer program mechanism comprising:

at least one set of probe settings including at least one gain parameter and corresponding to a predetermined operating characteristics for a particular probe;

a first set of instructions that receive a target temperature value;

a second set of instructions that receive a first probe setting corresponding to a desired set of operating characteristics for a probe;

a third set of instructions that select a set from the at least one set of probe settings in response to the first probe setting;

a fourth set of instructions that receive a sensed temperature value;

a fifth set of instructions that generate an error value by comparing the sensed temperature value to the target temperature value;

a sixth set of instructions that determine an output control value by applying a control function to the error value, the control function using the at least one gain parameter from the selected set; and a seventh set of instructions that cause an amount of power to be outputted to a thermal element in response to the output control value.

19. The computer program product of claim 18 wherein the at least one gain parameter of the at least one set of probe settings includes a set specific proportional gain factor and a set specific integral gain factor, and wherein:

the instructions that determine the output control value include instructions to:

generate a proportional value by multiplying the error value by the selected set specific proportional gain factor;

generate an integral signal by integrating the error value and multiplying the integrated error value by the selected set specific integral gain factor;

generate a derivative value by comparing the sensed temperature value to a previous sensed temperature value and applying a derivative function to generate an intermediate value and multiplying the intermediate value by a selected set specific derivative gain factor; and sum the proportional value, the integral value and the derivative value to generate the output control value.

20. The computer program product of claim 18 wherein the computer program mechanism further includes instructions to limit the output control value to a predetermined output value when the output control value exceeds a predetermined threshold.

21. The computer program product of claim 18 wherein the computer program mechanism further includes instructions to:

receive a switch setting corresponding to a particular profile at which to ramp up the output power; and change the target temperature value in response to the switch setting.

* * * * *

UNITED STATES PATENT AND TRADEMARK OFFICE
CERTIFICATE OF CORRECTION

PATENT NO. : 6,162,217
DATED : December 19, 2000
INVENTOR(S) : Donald P. Kannenberg and Andrew I. Lisiecki

It is certified that error appears in the above-identified patent and that said Letters Patent is hereby corrected as shown below:

<u>Title page,</u>
Item [56], References Cited, U.S. PATENT DOCUMENTS,
After "6,074,386   6/2000   Goble et al. ................. 606/34" insert the following:

|  |  |  |  |
|---|---|---|---|
| -- 5,743,903 | 4/1998 | Stern et al. ............... | 606/31 |
| 5,697,925 | 12/1997 | Taylor .................... | 606/34 |
| 5,496,312 | 3/1996 | Klicek .................... | 606/34 |
| RE35,330 | 9/1996 | Malone et al. ............ | 606/28 --. |

Signed and Sealed this

Thirty-first Day of December, 2002

JAMES E. ROGAN
*Director of the United States Patent and Trademark Office*